(12) United States Patent
Anstadt

(10) Patent No.: US 11,896,812 B1
(45) Date of Patent: Feb. 13, 2024

(54) VERSATILE MODULAR HEART PUMP FOR NON-BLOOD CONTACTING VENTRICULAR FUNCTION AUGMENTATION

(71) Applicant: Lifebridge Technologies, LLC, Dayton, OH (US)

(72) Inventor: Mark P. Anstadt, Kettering, OH (US)

(73) Assignee: Lifebridge Technologies LLC, Dayton, OH (US)

( * ) Notice: Subject to any disclaimer, the term of this patent is extended or adjusted under 35 U.S.C. 154(b) by 0 days.

(21) Appl. No.: 18/160,963

(22) Filed: Jan. 27, 2023

(51) Int. Cl.
- A61M 60/148 (2021.01)
- A61M 60/20 (2021.01)
- A61M 60/191 (2021.01)

(52) U.S. Cl.
CPC .......... *A61M 60/148* (2021.01); *A61M 60/20* (2021.01); *A61M 60/191* (2021.01)

(58) Field of Classification Search
CPC ... A61M 60/148; A61M 60/20; A61M 60/191
See application file for complete search history.

(56) References Cited

U.S. PATENT DOCUMENTS

| | | | |
|---|---|---|---|
| 2,826,193 A | 3/1958 | Vineberg |
| 2,889,780 A | 6/1959 | Binford |
| 3,053,249 A | 9/1962 | Smith |
| 3,233,607 A | 2/1966 | Bolle |
| 3,279,464 A | 10/1966 | Kline |
| 3,304,501 A | 2/1967 | Ruthenberg |
| 3,371,662 A | 3/1968 | Heid |
| 3,376,863 A | 4/1968 | Kolobow |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Schiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,536,893 A | 8/1985 | Parravicini |
| 4,609,176 A | 9/1986 | Powers |
| 4,621,617 A | 11/1986 | Sharma |
| 4,662,358 A | 5/1987 | Farrar |
| 4,684,143 A | 8/1987 | Sata |
| 4,957,477 A | 9/1990 | Lundback |

(Continued)

*Primary Examiner* — Lindsey G Wehrheim
(74) *Attorney, Agent, or Firm* — LaMorte & Associates, P.C.

(57) ABSTRACT

A system and method for positioning a modular heart pump about the ventricles of the heart. The modular heart pump has at least one active panel and an apical base. Each active panel includes an inflatable membrane. The apical base helps retain the active panels on position about the heart. The components are assembled in vivo to create a pump assembly that encircles all or part of the heart. During installation, the active panels are advanced along the outside of the ventricles. Suction is provided on the leading edge of the active panels to remove any fluids and/or loose tissue that may prevent the active panel from advancing to an operable position.

24 Claims, 15 Drawing Sheets

(56) References Cited

U.S. PATENT DOCUMENTS

| | | | |
|---|---|---|---|
| 4,979,936 A | 12/1990 | Stephenson |
| 5,066,111 A | 11/1991 | Inokuchi |
| 5,089,017 A | 2/1992 | Young |
| 5,098,369 A | 3/1992 | Heilman et al. |
| 5,098,442 A | 3/1992 | Grandjean |
| 5,119,804 A | 6/1992 | Anstadt |
| 5,131,905 A | 7/1992 | Grooters |
| 5,156,154 A | 10/1992 | Valenta, Jr. et al. |
| 5,158,978 A | 10/1992 | Rubin |
| 5,169,381 A | 12/1992 | Snyders |
| 5,199,804 A | 4/1993 | Rimbey et al. |
| 5,205,722 A | 4/1993 | Hammond |
| 5,256,132 A | 10/1993 | Snyders |
| 5,273,518 A | 12/1993 | Lee et al. |
| 5,322,067 A | 6/1994 | Prater |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A | 2/1998 | Rosenberg et al. |
| 5,716,379 A | 2/1998 | Bourgeios et al. |
| 5,738,627 A | 4/1998 | Kovacs et al. |
| 5,749,839 A | 5/1998 | Kovacs |
| 5,769,800 A | 6/1998 | Gelfand et al. |
| 5,800,334 A | 9/1998 | Wilk |
| 5,861,558 A | 1/1999 | Buhl et al. |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A | 10/1999 | Tsitlik et al. |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,238,334 B1 * | 5/2001 | Easterbrook, III . A61M 60/468 600/16 |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez et al. |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness et al. |
| 6,508,756 B1 * | 1/2003 | Kung .................. A61M 60/865 600/37 |
| 6,540,659 B1 | 4/2003 | Milbocker |
| 6,547,716 B1 | 4/2003 | Milbocker |
| 6,572,534 B1 | 6/2003 | Milbocker et al. |
| 6,602,182 B1 | 8/2003 | Milbocker |
| 6,612,978 B2 | 9/2003 | Lau et al. |
| 6,616,596 B1 | 9/2003 | Milbocker |
| 6,622,045 B2 | 9/2003 | Snell et al. |
| 6,626,821 B1 | 9/2003 | Kung et al. |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,808,483 B1 | 10/2004 | Ortiz et al. |
| 6,846,296 B1 | 1/2005 | Milbocker et al. |
| 6,971,127 B2 | 12/2005 | Richards |
| 7,331,221 B2 | 2/2008 | Wise et al. |
| 7,494,459 B2 | 2/2009 | Anstadt et al. |
| 7,871,366 B2 | 1/2011 | Criscione et al. |
| 8,187,160 B2 | 5/2012 | Criscione et al. |
| 10,463,496 B2 | 11/2019 | Criscione et al. |
| 11,511,102 B2 | 11/2022 | Criscione et al. |
| 2003/0032855 A1 | 2/2003 | Shahinpoor |
| 2004/0010180 A1 | 1/2004 | Scorvo |
| 2004/0024315 A1 | 2/2004 | Chalana |
| 2004/0059183 A1 | 3/2004 | Jozef et al. |
| 2004/0078067 A1 | 4/2004 | Thompson et al. |
| 2004/0102674 A1 | 5/2004 | Zadini et al. |
| 2004/0116769 A1 | 6/2004 | Jassawalla |
| 2004/0167375 A1 | 8/2004 | Couvillon |
| 2004/0225177 A1 | 11/2004 | Coleman et al. |
| 2004/0267086 A1 | 12/2004 | Anstadt et al. |
| 2005/0113632 A1 | 5/2005 | Ortiz et al. |
| 2005/0148814 A1 | 7/2005 | Fischi et al. |
| 2005/0234289 A1 | 10/2005 | Anstadt et al. |
| 2006/0142634 A1 | 6/2006 | Anstadt et al. |
| 2006/0167334 A1 | 7/2006 | Anstadt et al. |
| 2006/0211909 A1 | 9/2006 | Anstadt et al. |
| 2007/0197859 A1 | 8/2007 | Schaer et al. |
| 2008/0257412 A1 | 10/2008 | Gordon |
| 2010/0152523 A1 | 6/2010 | MacDonald et al. |
| 2011/0196189 A1 | 8/2011 | Milbocker |
| 2015/0080640 A1 | 3/2015 | Lillehel |
| 2016/0101230 A1 | 4/2016 | Ochsner |

* cited by examiner

VERSATILE MODULAR HEART PUMP FOR NON-BLOOD CONTACTING VENTRICULAR FUNCTION AUGMENTATION

BACKGROUND OF THE INVENTION

1. Field of the Invention

In general, the present invention relates to the structure of heart pumps of the type that physically apply forces to the heart and assist the heart in pumping. More particularly, the present invention relates to a heart pump system designed for versatile installation in order to augment ventricular systolic and diastolic function.

2. Prior Art Description

Many patients can benefit from the use of a pneumatic heart pump. Pneumatic heart pumps have cups or cuffs that are placed around all or part of the heart's ventricles. The pneumatic heart pump contains expandable bladders that selectively inflate and deflate in rhythm with the heart. As the bladders inflate and deflate, they assist the pumping function of the heart. The heart pumps are connected to external drives that provide air pressure to selectively inflate and deflate the bladders. Such heart pump systems are exemplified by U.S. Patent Application Publication No. 2005/0234289 to Anstadt and U.S. Patent Application Publication No. 2006/0167334 to Anstadt.

Since such heart pump devices are generally designed to fit around the ventricles of the surgically exposed heart, the heart pump requires surgical procedures where an opening is cut through the breastbone and/or ribs for installation. However, open surgeries have many inherent problems. Open surgery is highly invasive and can result in significant complications such as blood loss, pain, inflammatory responses and infection. Therefore, open surgical procedures can require more post-operative care, longer hospital stays, and longer recovery.

It is for these and other reasons that many physicians and patients prefer minimally invasive surgical procedures. Minimally invasive surgeries involve smaller incisions. When approaching the heart the intercostal space is the limited factor. Generally, instruments and devices have small and/or flexible constructs so that they can be passed into the chest cavity when performing minimally invasive procedures on the heart.

One obvious problem is that pneumatic heart pumps can be too large to use in minimally invasive procedures. The result is that the surgical opening must be enlarged by spreading or cutting the ribs. Consequently, the procedure becomes more invasive than desired. This problem can be addressed in two ways. First, a small or partial heart pump can be used that is small enough to pass through the minimally invasive incision. A smaller heart pump may fit through the incision but may not be as would a full sized heart pump. Therefore, a second alternative is use of a collapsible heart pump. Such heart pumps may have a mesh framework that can be drawn into a thorascopic insertion tube and advanced into the body. Once in the body, the mesh framework expands as it is expelled from the thorascopic insertion tube. The expanded shape is large enough to encircle at least part of the heart. Such prior art devices are exemplified by U.S. Pat. No. 10,463,496 to Criscone and U.S. Pat. No. 11,511,102 to Criscone.

One of the problems with undersized heart pumps and expanding heart pumps is that they are advanced onto the heart from the apex to the base of the ventricles. This application orientation may be to perform in a minimally invasive procedure. Furthermore, since the heart pump is applied and seated over the apex of the ventricles, there is a tendency for such heart pumps to work themselves off the ventricles. The repeated expansion and contraction of the bladders generate peristaltic forces that encourage the heart pump to move off the heart. The result is that continuous effort must be used to secure the pump on the heart. Furthermore, heart pumps are more effective when they apply augmentation forces in the mid to basilar regions of the heart instead of the apex.

Another problem with prior art heart pumps that are intended for a minimally invasive procedure is that the heart pumps need to be positioned around the heart. A heart pump can only be positioned around a heart if there is no scar tissue present or other obstacles caused by disease or prior therapeutic procedures, such as coronary bypass or heart valvular surgeries. Many people who need pneumatic heart pumps have had earlier heart procedures that create scar tissue or other obstacles. These obstacles can significantly impair a heart pump from being placed around the heart. As such, a heart pump designed to encircle the heart may frequently be unusable or ineffective.

A need therefore exists for an improved heart pump system that has the design characteristics and operational performance to act on the heart's surface and can also be installed in a minimally invasive surgical procedure. A need also exists for an improved heart pump where the pumping action of the heart pump does not bias the heart pump away from the heart. A need further exists for a heart pump that can be applied to a heart that has prior scarring or obstacles that prevent the heart pump from being properly applied to the heart's surface. Lastly, a need exists for a heart pump that can properly translate forces to the heart and result in optimal ventricular strain dynamics that both improve pump function and facilitate myocardial recovery. These needs are met by the present invention as described and claimed below.

SUMMARY OF THE INVENTION

The present invention is a system and method for positioning a modular heart pump about the ventricles of the heart. The modular heart pump has at least one active panel. Each active panel includes an inflatable membrane. The active panels are elastomeric and can be collapsed for installation in a minimally invasive fashion. The active panels are inserted around the heart's surface. Likewise, an apical hub and panel connectors are inserted to complete the device construct. The active panels, apical hub, and panel connectors are assembled in vivo to create an assembly that encircles all or part of the heart.

During installation, the active panels are advanced along the outside of the ventricles. Suction is provided on the leading edge of the active panels to remove any fluids and/or loose tissue that may prevent the active panel from advancing to an operable position.

Once positioned about the ventricles, pneumatic pressure is supplied to the active panels. The active panels contain inflatable membranes that selectively inflate and deflate to assist in the pumping action of the heart. The suction provided through the apical hub fundamental to maintaining a seal between the heart and modular assembly resulting in effective diastolic expansion of the heart. Optional sensors, such as an ultrasonic scan head can be positioned in the apical head. The scan head is biased against the apex of the ventricles by the suction being applied through the apical hub. In this position, the scan head is optimally positioned to electronically monitor the translate forces being applied to the heart and the resulting ventricular strain dynamics that benefit pump function and myocardial recovery.

The active panels can also contain sensors that measure the ventricular strain dynamics being applied to the heart. Using the output of the sensors, one or more active panels can be selectively inflated and deflated. When more than one active panel is instituted, the pneumatic actuation of the other panels can be varied as to provide variation in the relevant regions of compression/expansion. This design feature allows variations in regional cardiac assist pertinent to variations of cardiac function that may occur in separate regions of the heart.

BRIEF DESCRIPTION OF THE DRAWINGS

For a better understanding of the present invention, reference is made to the following description of exemplary configurations thereof, considered in conjunction with the accompanying drawings, in which.

DETAILED DESCRIPTION OF THE DRAWINGS

Although the present invention system is modular and can be configured in different ways, only a few configurations are illustrated. The exemplary configurations are being shown for the purposes of explanation and description. The exemplary configurations are selected in order to set forth some of the best modes contemplated for the invention. The illustrated configurations, however, are merely exemplary and should not be considered as limitations when interpreting the scope of the appended claims.

Figure 1:
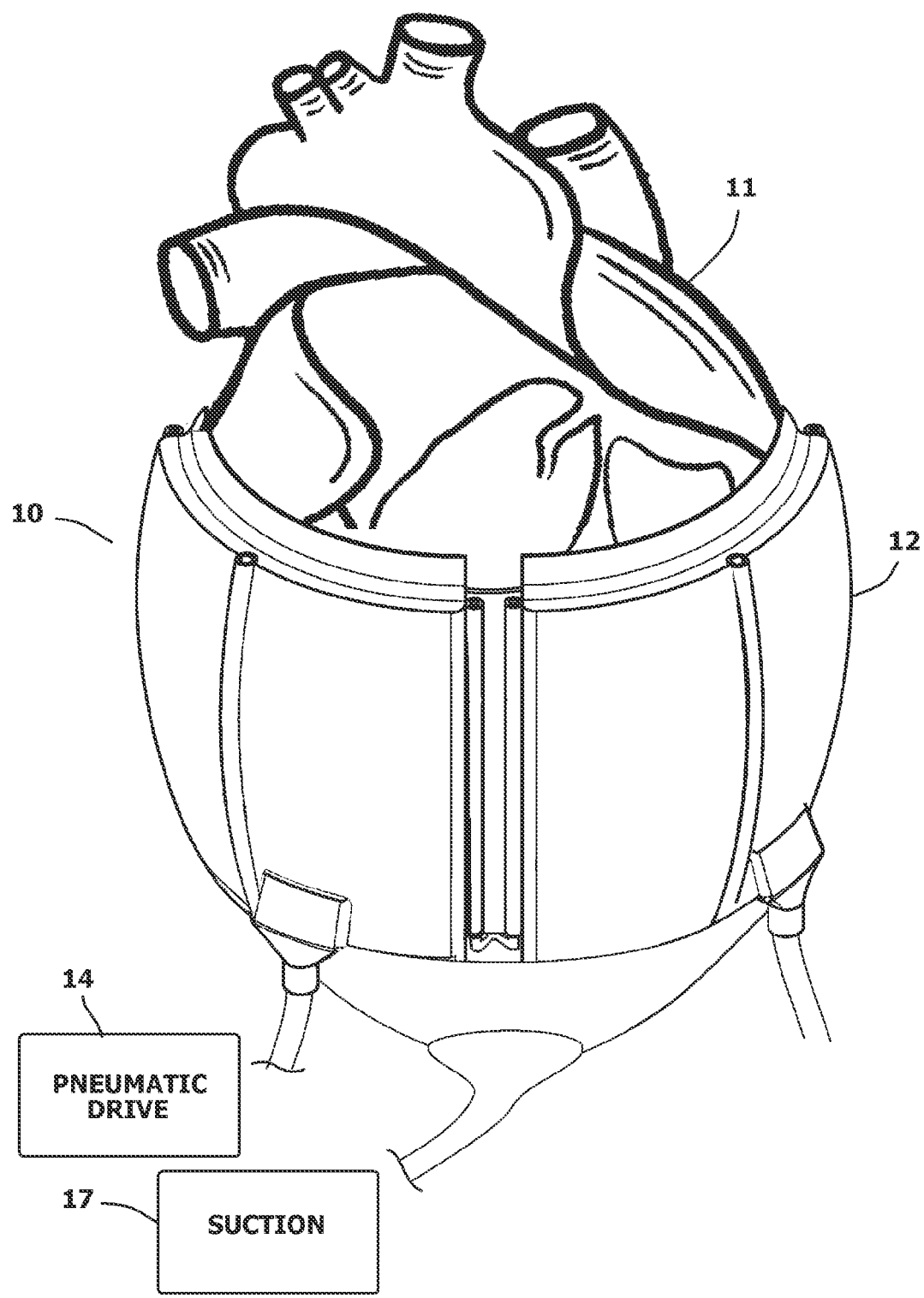
FIG. 1 shows an exemplary embodiment of a heart pump system containing a modular assembly, wherein the heart pump system is shown in conjunction with a heart.

Referring to FIG. 1, a heart pump system 10 is shown that helps a heart 11 pump blood. The heart pump system 10 has an external automated drive 14 that selectively applies positive and negative pneumatic pressure to a modular assembly 12. The heart 11 has measurable dimensions that are unique for a particular individual or condition. One of the measurable dimensions is the maximal outer surface diameter of the heart in its short axis. The maximal diameter corresponds to the outer diameter of the ventricular myocardium as measured at the end of the diastolic cycle. Likewise, the heart 11 has a measurable length that corresponds to the length of the ventricles at the end of the diastolic cycle. These dimensions of the heart 11 can be readily obtained from various medical scanning equipment, such as x-rays, ultrasounds, MRIs, and the like. Furthermore, it is understood that the heart 11 has a heartbeat, wherein the heart 11 contracts with a periodic rhythm. Although the rhythm can be regular or irregular, it has a general optimal range of contractions over increments of time. The rhythm of the heart 11 can also be quantified using heart monitoring equipment, such as a blood pressure monitor or an ECG unit.

The embodiment of the modular assembly 12 shown in FIG. 1 is configured to fit partially or completely around the ventricles of the heart 11. Accordingly, the modular assembly 12 is sized to receive the maximum diameter and the ventricle length of the heart 11. As will later be explained, the modular assembly 12 can be configured multiple ways. This enables the modular assembly 12 to be configured to encircle the ventricles in full or to only surround a portion of the ventricles. In this manner, the modular assembly 12 can be installed despite scar tissue and other obstacles that may be present on and around the heart 11.

Figure 2:
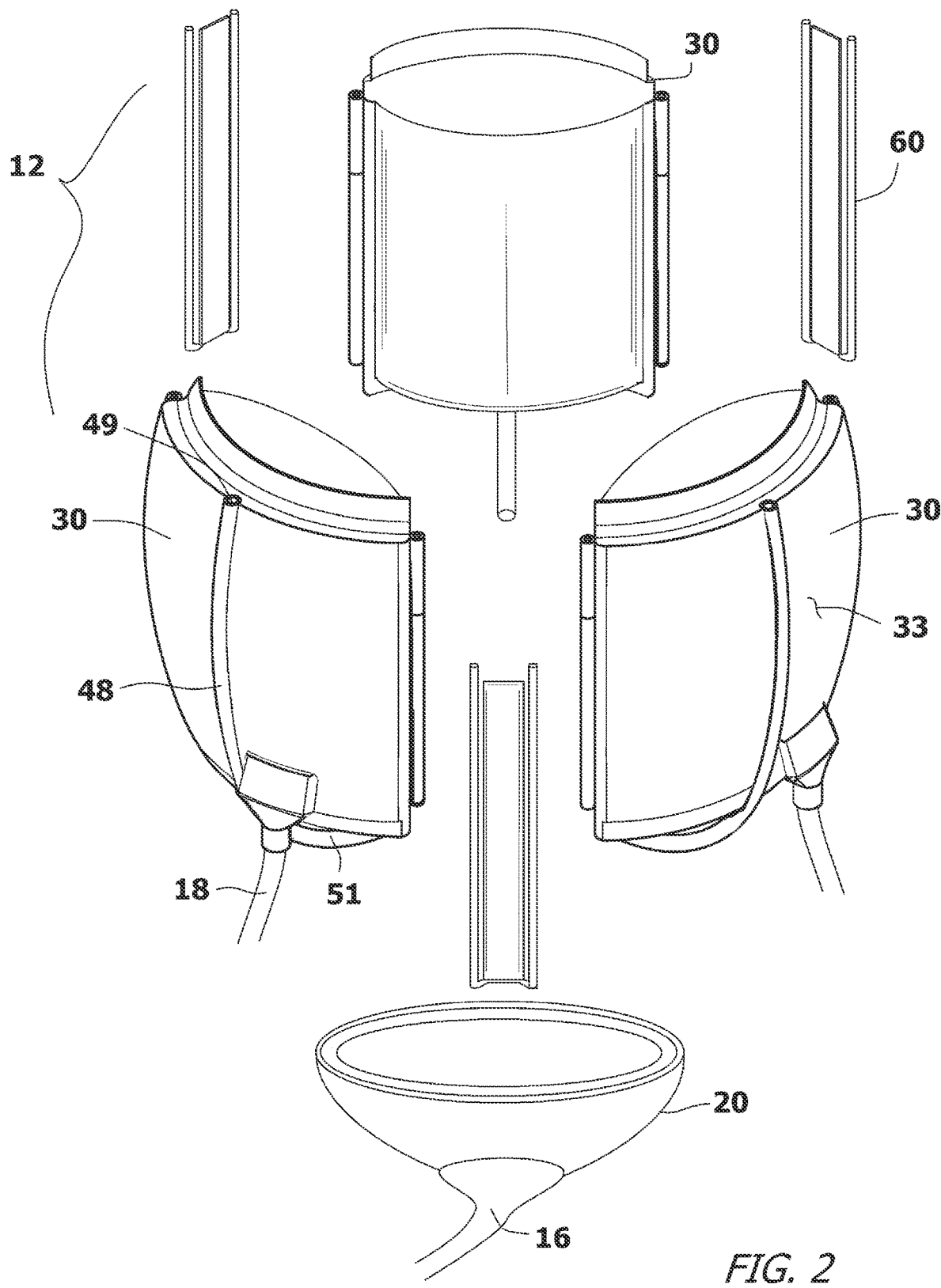
FIG. 2 is an exploded view of the modular assembly shown in FIG. 1.

Referring to FIG. 2 in conjunction with FIG. 1, it can be seen that the modular assembly 12 is made of different components that are inserted into the body separately and assembled in vivo around the heart 11. The various components are shaped, sized, and constructed to be insertable around the heart through small incisions using minimally invasive techniques. The device can also be installed when the heart is fully exposed during open heart surgery using a sternotomy or other open approaches such as a thoracotomy. The modular assembly of the device provides similar functionality when used with a minimally invasive versus a standard open surgical approach.

The major components of the modular assembly 12 include an apical hub 20, active panels 30, and panel connectors 60. The apical hub 20 is connected to a negative pressure tube 16 that extends out of the body. The active panels 30 are positioned above the apical hub 20. The active panels 30 are connected to pneumatic drive tubes 18. The pneumatic drive tubes 18 connect to the external drive equipment 14 that controls the pneumatic pressures supplied to the active panels 30. The negative pressure tube 16 leads to suction 17 that facilitates device installation, attachment and diastolic assist.

Figure 3:
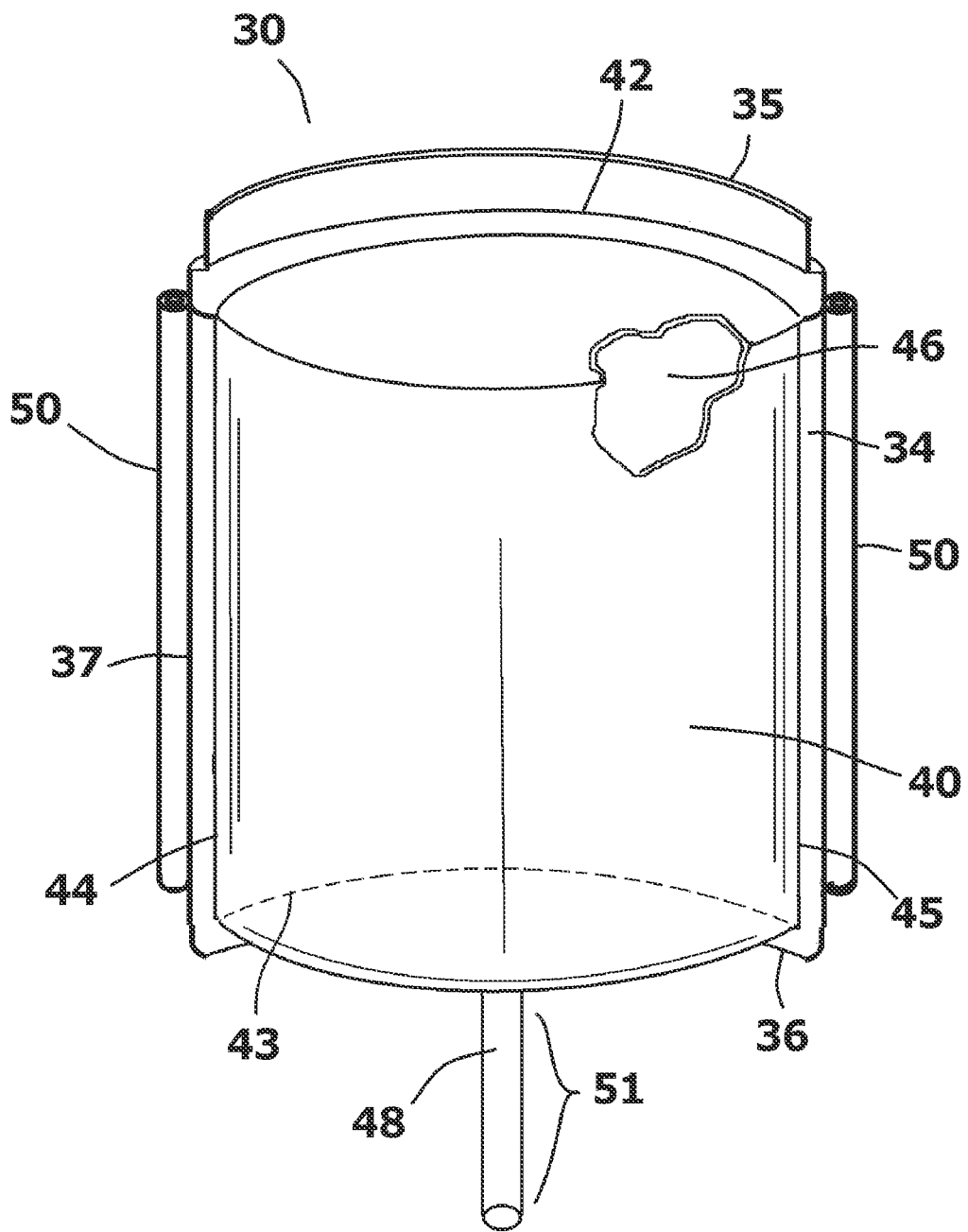
FIG. 3 is a fragmented view of an active panel and apical hub used in the modular assembly of FIG. 2.
Figure 4:
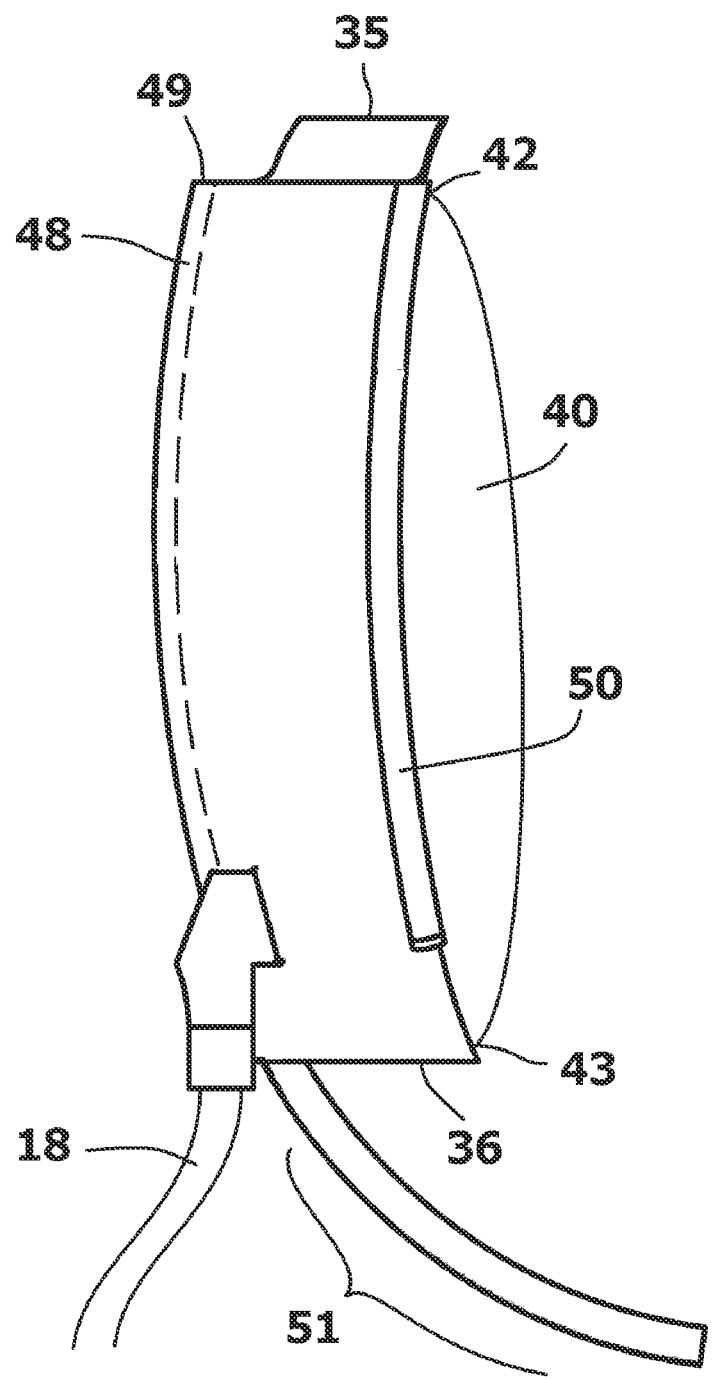
FIG. 4 is a cross-sectional view of an active panel and apical hub used in the modular assembly of FIG. 2.

The active panels 30 are used to apply mechanical forces to the heart 11. Referring to FIG. 3 and FIG. 4 in conjunction with FIG. 1 and FIG. 2, it can be seen that each active panel 30 has a shell wall 32. The shell wall 32 has an exterior surface 33, an interior surface 34, a basal edge 35, an apical edge 36 and side edges 37, 38. An inflatable membrane 40 is affixed to the interior surface 34. The inflatable membrane 40 is affixed to the shell wall 32 along a basal attachment seam 42, an apical attachment seam 43, and side seams 44, 45. An air compartment 46 is defined between the basal attachment seam 42, the apical attachment seam 43, the side seams 44, 45, and the shell wall 32. As air is added to and released from the air compartment 46, the inflatable membrane 40 is free to expand and contract in an elastic manner. The pneumatic drive tube 18 communicates with the air compartment 46 between the shell wall 32 and the inflatable membrane 40. The inflatable membrane 40 is selectively inflated and deflated by air flowing through the pneumatic drive tube 18 into, and out of, the air compartment 46.

Connection conduits 50 are provided near the side edges 37, 38 of the shell wall 32. The connection conduits 50 can be formed through the shell wall 32 or through tubes that are affixed to the shell wall 32. The connection conduits 50 provide openings that extend from the basal edge 35 of the shell wall 32 to the apical edge 36 of the shell wall 32.

A suction tube 48 is affixed to the exterior surface 33 of the shell wall 32. The suction tube 48 can be integrated into the structure of the shell wall 32 or can be a separate component affixed to the shell wall 32. The suction tube 48 has an intake end 49 that is exposed at or near the basal edge 35 of the shell wall 32. The suction tube 48 extends down the length of the shell wall 32 and continues beyond the apical edge 36 of the shell wall 32. This produces a free section 51 of the suction tube 48 that extends away from the active panel 30. The suction tube 48 is used during the surgical insertion process, as is later explained in the description of the insertion methodology.

The entirety of the active panel 30 is made from elastomeric material, such as silicone. Accordingly, the active panel 30 is capable of being collapsed for minimally invasive insertion using minimally invasive techniques. This enables each active panel 30 to be separately advanced through a small incision and placed around the surface of the heart. Once freed from a thorascopic insertion tube, the resiliency of the elastomeric material automatically returns each active panel 30 to its original shape and size.

Figure 5:
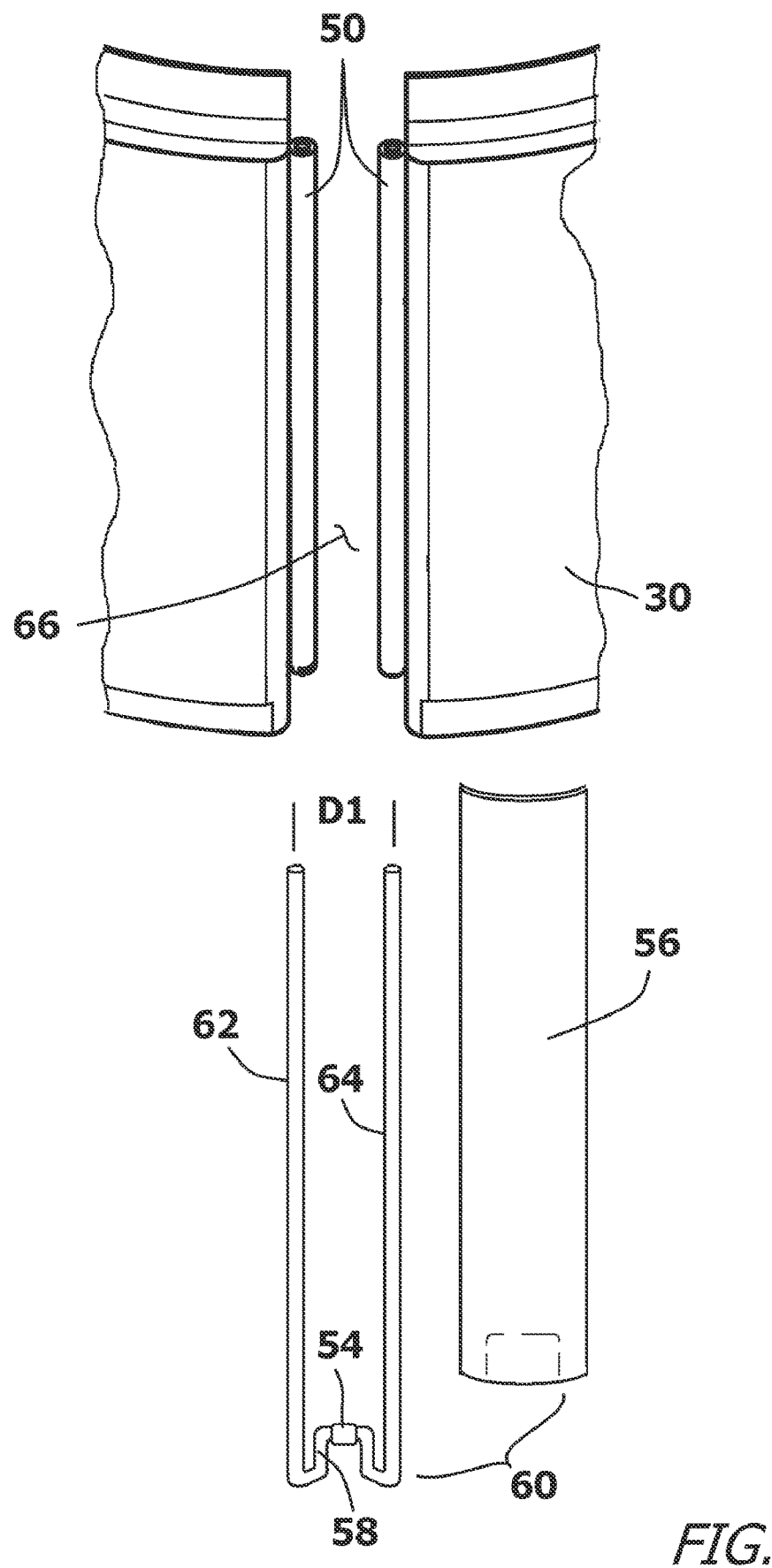
FIG. 5 is fragmented view of the modular assembly showing two adjacent active panels and an exploded view of a panel connector.
Figure 6:
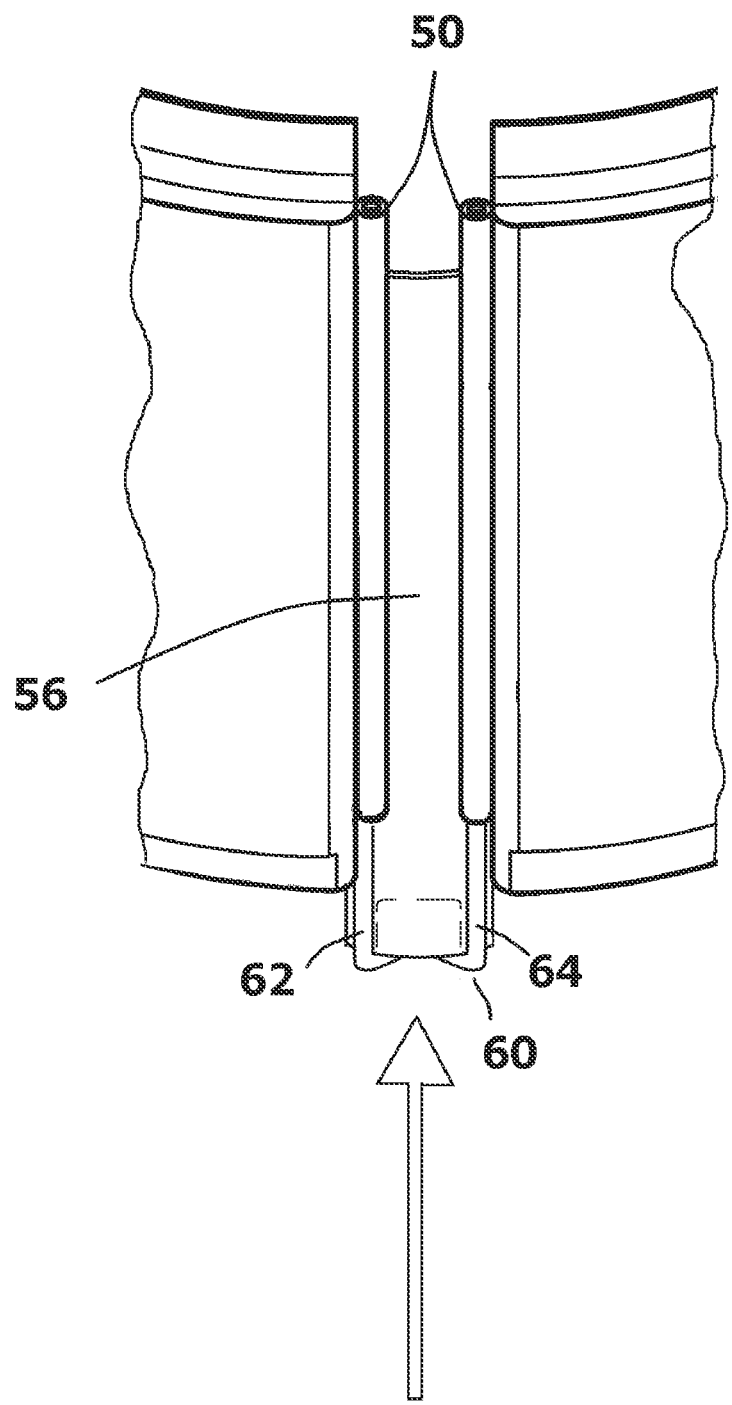
FIG. 6 is a fragmented view of the modular assembly showing two adjacent active panels being joined by a panel connector.

The active panels 30 are modular. Accordingly, two or more active panels 30 can be interconnected around the heart. Referring to FIG. 5 and FIG. 6, in conjunction with FIG. 2 and FIG. 3, it can be seen that the connection conduits 50 on adjacent shell walls 32 of active panels 30 are interconnected using panel connectors 60. Each panel connector 60 has two primary pins 62, 64. The pins 62, 64 can be pre-contoured to match the desired contour of the outer shell. The primary pins 62, 64 are preferably parallel but can be offset by up to ten degrees. The primary pins 62, 64 are spaced apart by a minimum distance D1. This minimum distance D1 can be purposely varied for different panel connectors 60 for reasons described below. Each of the primary pins 62, 64 is sized to pass into the connection conduits 50 on the active panels 30. By passing the primary pins 62, 64 into the connection conduits 50 of two adjacent active panels 30, the two active panels 30 are mechanically joined. A gap space 66 exist between adjacent active panels 30. The size of the gap space 66 between the joined active panels 30 is determined by the minimum distance D1 between the primary pins 62, 64. In this manner, the maximum circumference of the modular assembly 12 can be selectively altered. Panel connectors 60 with short distances between primary pins 62, 64 can be used on hearts with small myocardium diameters. Panel connectors 60 with large distances between primary pins 62, 64 can be used on hearts with larger myocardium diameters.

Within the structure of each panel connector 60, the primary pins 62, 64 are interconnected by a lateral bridge 58. The overall length of the lateral bridge 58 determines the minimum distance D1 between the primary pins 62, 64. The lateral bridge 58 interconnects to, and supports, a gap shield 56. The gap shield 56 has elastomeric characteristics similar to the shell and has a width W1 that is wider than the distance D1 between primary pins 62, 64. The gap shield 56 is held at a position that is between or slightly offset from the primary pins 62, 64. As a consequence, when the primary pins 62, 64 are advanced into the connection conduits 50 of adjacent active panels 30, the gap shield 56 can extends between, over or behind the connection conduits 50 of the adjacent active panels 30, therein covering the gap space 66. The width W1 of the gap shield 56. When properly sized, is wide enough to cover the gap space 66, yet is narrow enough not to interfere with the inflatable membranes 40 on the inside of the active panels 30. In this manner, the gap shields 56 do not inhibit any expansion or contraction of the inflatable membranes 40.

An optional strain sensor 54 can be attached to the lateral bridge 58 of the panel connector 60. The strain sensor 54 measures the bending and torsional strains being experienced by the primary pins 62, 64. The data collected by the strain sensors 54 can be used to regulate the air pressure differentials supplied to each of the active panels 30 in a manner that enables the active panels 30 to better assist the heart 11 in pumping.

Figure 7:
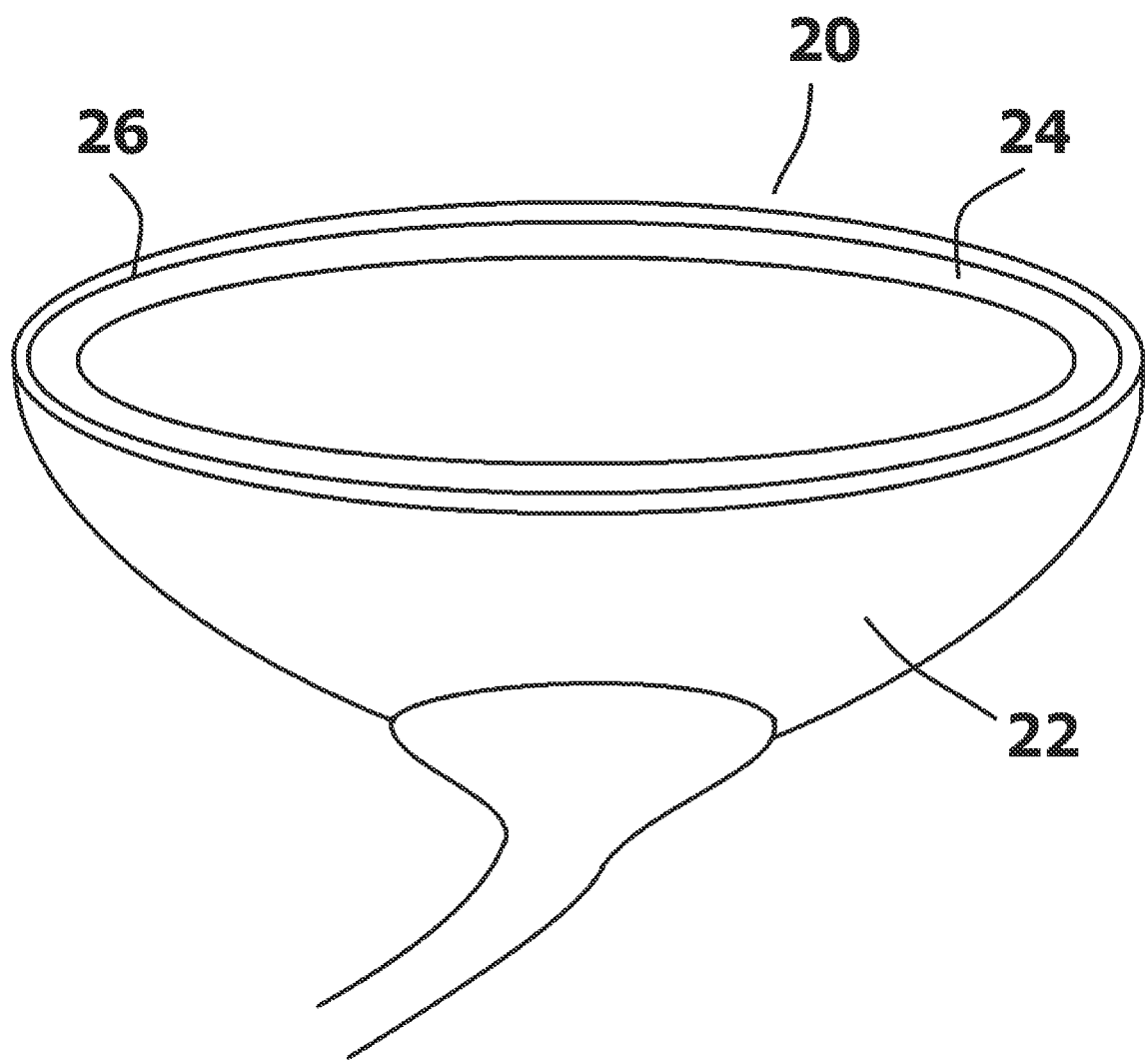
FIG. 7 is an enlarged view of the apical hub used in the modular assembly of FIG. 2.

Referring to FIG. 7 in conjunction with FIG. 2, it will be understood that the apical hub 20 is made from elastomeric material. The apical hub 20 has a semi-spherical concave/convex body 22 that presents a circular rim 24 toward the active panels 30. Lip elements 26 can be formed on the circular rim 24 to help engage the active panels 30 and connection panels 60. The apical hub 20 is made from elastomeric material, such as silicone, and is capable of being collapsed for insertion using a minimally invasive procedure. Accordingly, a collapsed apical hub 20 can be advanced through a small incision and released on the apex of the heart. Once the apical hub 20 is in position it is opposed against the modular components and vacuum facilitates proper integration of these components. The resiliency of the elastomeric material further returns the apical hub 20 to its original shape and size.

Figure 8:
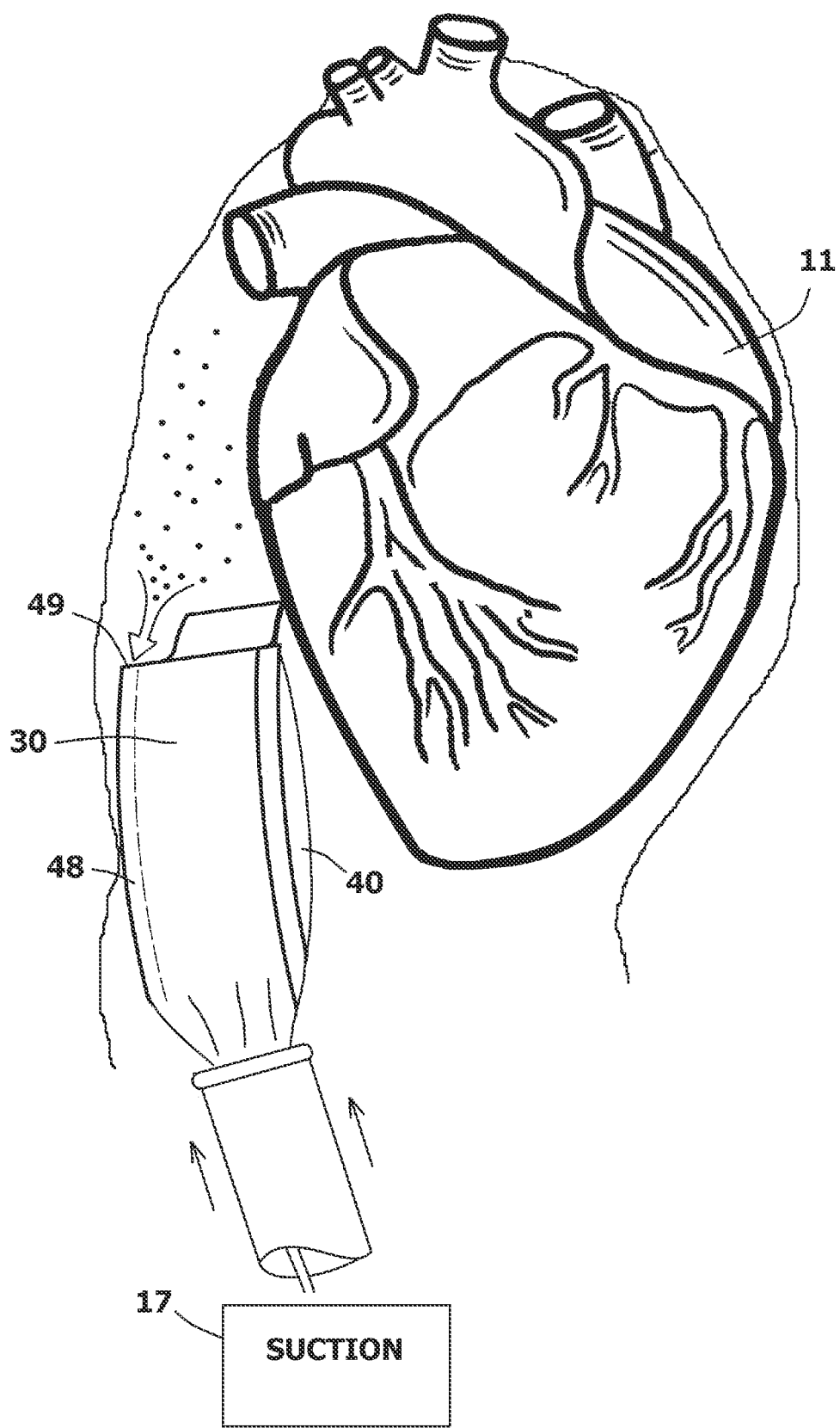
FIG. 8 shows an active panel being inserted around the heart.
Figure 9:
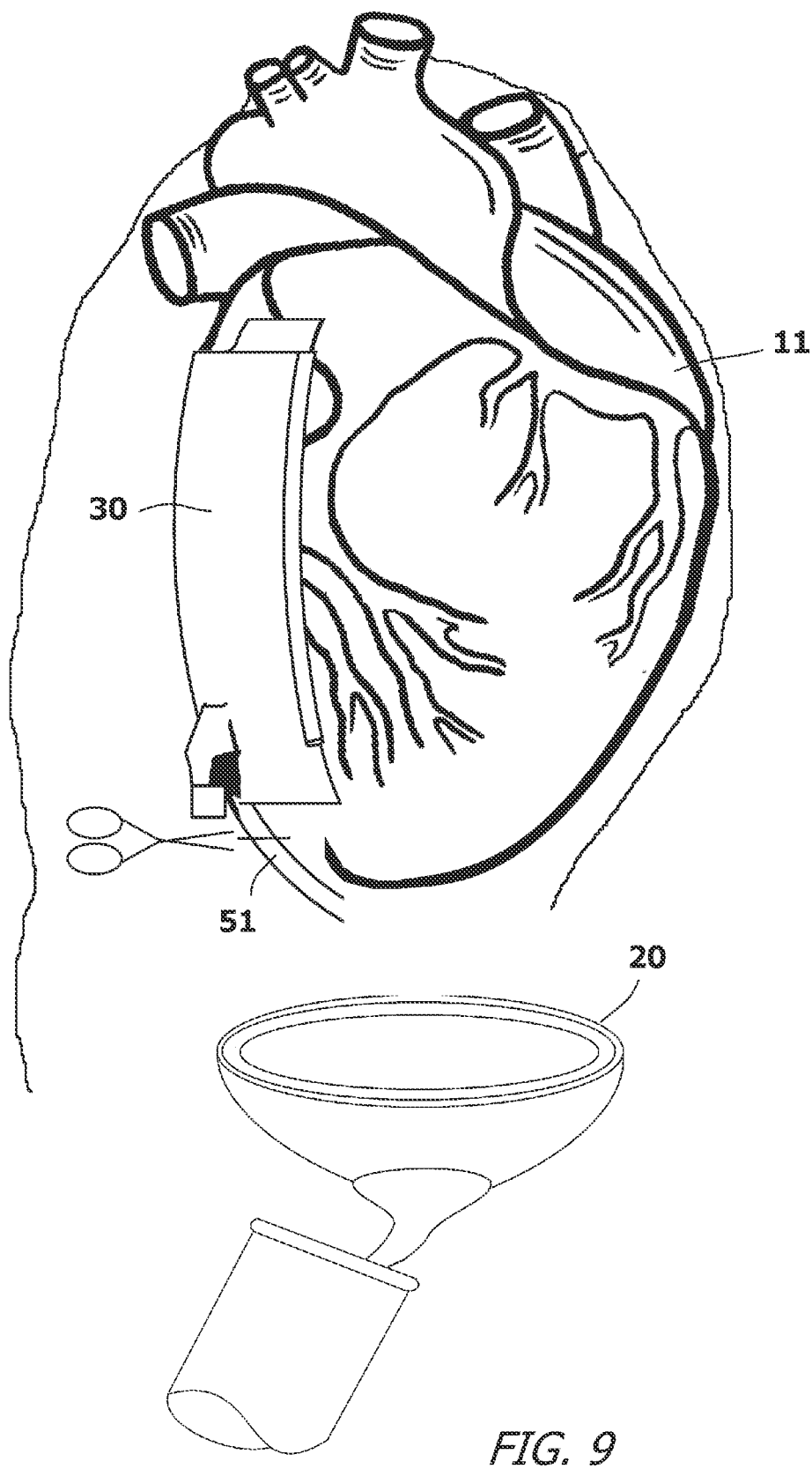
FIG. 9 shows an apical hub being inserted over the apex of the heart.

Referring to FIG. 8 and FIG. 9 in conjunction with FIG. 4 and FIG. 2, it will be understood that a surgical team selects a modular assembly 12 that is proper for the size of the heart 11. The selection of the modular assembly 12 includes the selection of the panel connectors 60 with the proper width for the myocardium of the heart 11. Once the proper size is selected, the free section 51 of the suction tube 48 on the active panel 30 is connected to an external suction drain 17. The negative pressure from the external suction 17 is forwarded to the intake end 49 of the suction tube 48 on the top edge 35 of the active panel 30. The active panel 30 is advanced around the heart's surface while still being connected to the external suction 17. Using a small incision, the active panel 30 is inserted around the heart using available minimally invasive techniques. As the active panel 30 is advanced, any fluids encountered by the advancing active panel 30 are drawn into the intake end 49 of the suction tube 48. In this manner, the advancing active panel 30 clears its own path as it is advanced. The active panel 30 is advanced on to the surface of the heart. Once released, the active panel 30 automatically expands to its normal size and configuration. The active panel 30 is then further advanced into its operational position using minimally invasive retractors and similar instruments.

As the active panel 30 is being set into its operational position. The inflatable membrane 40 on the active panel 30 can be partially or fully inflated and deflated in a repeating cycle. This inflation/deflation cycle helps displace tissue and fluids within the pericardial cavity and assists the active panel 30 in reaching its operational position. Once the active panel 30 has reached its operational position, then the free section 51 of the suction tube 48 can be detached or severed from the active panel 30.

If there is room around the heart 11 for more than one active panel 30 and the surgical team wants to use more than one active panel 30, then the installation step is repeated until multiple active panels 30 are present in the pericardial cavity. In FIG. 1 and FIG. 2, a full 360 degree construct can be created using just three active panels 30. It will be understood that such sizing is exemplary and that the widths of the active panels 30 can be altered so that between two and six active panels 30 are required to create a full 360 degree construct.

As the active panels 30 are inserted, they are interconnected using the panel connectors 60. Once the active panels 30 are positioned about the heart 11 and are interconnected, the apical hub 20 is inserted using available minimally invasive techniques. The apical hub 20 is then connected to each of the active panels 30 to complete the modular assembly 12.

Figure 10:
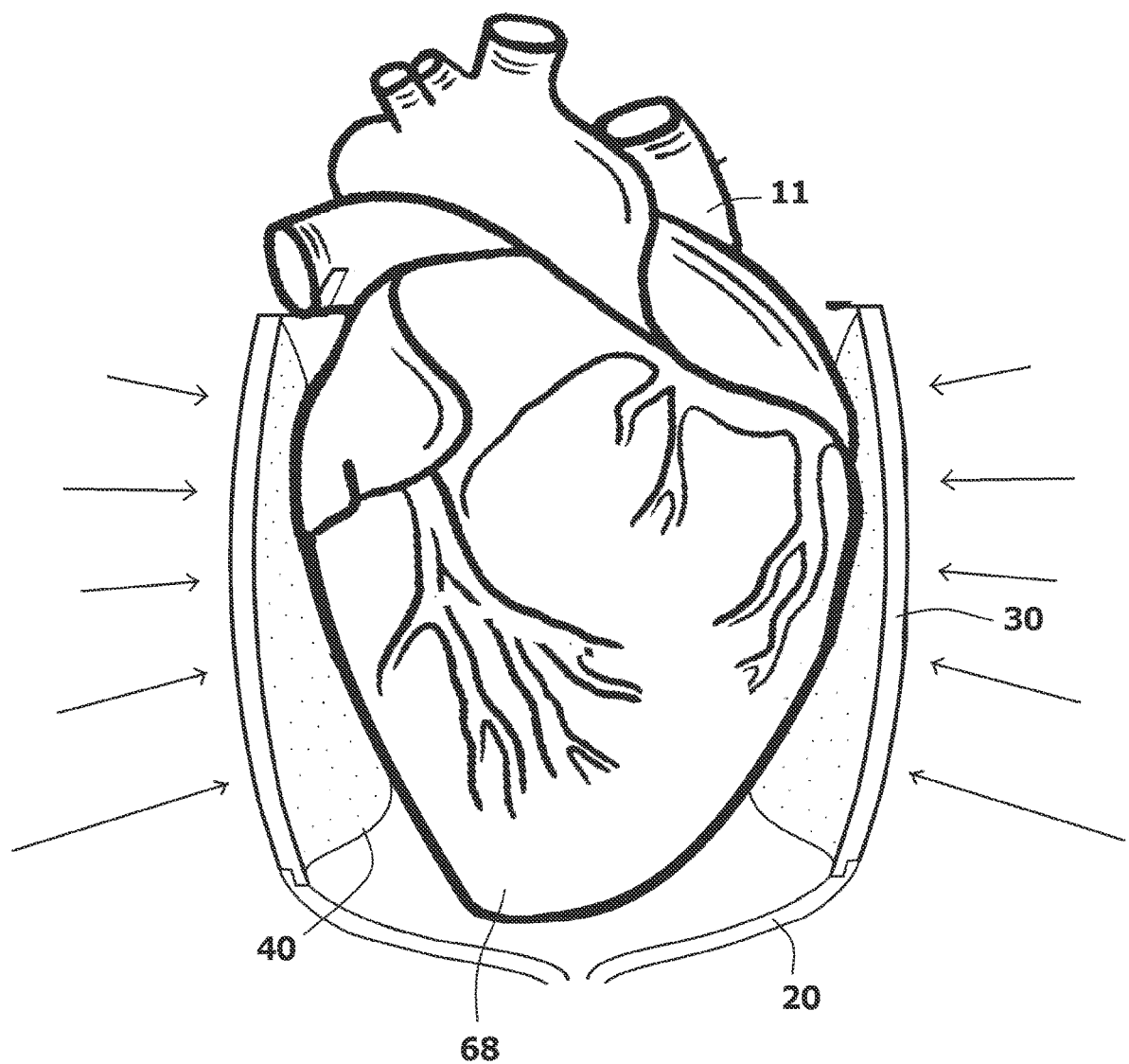
FIG. 10 is a cross-sectional view of the modular assembly in a loaded condition applying forces to the heart.

Referring to FIG. 10, it can be seen that the apical hub 20 holds the active panels 30 in position well above the ventricle apex 68 at the bottom of the heart 11. As such, the active panels 30 act upon the heart 11 in the areas of the heart 11 that are not sharply tapered. Since the inflatable membranes 40 are highly flexible, they mostly conform to the shape of the heart 11 as they apply forces, shown by arrows, to the heart 11. The result is that the forces are mostly even across the full area of contact between the inflatable membranes 40 and the heart 11. The evenness of the force application on the upper two thirds of the heart facilitates optimal pump function of the ventricles without creating the tendency for the modular assembly to come off of the heart or migrate in an apical direction. The vacuum delivered through the apical hub 20 maintains device apposition on the heart while facilitating diastolic assist. Consequently, the modular assembly 12 will optimize ventricular pump function while staying in the proper location as installed.

Figure 11:
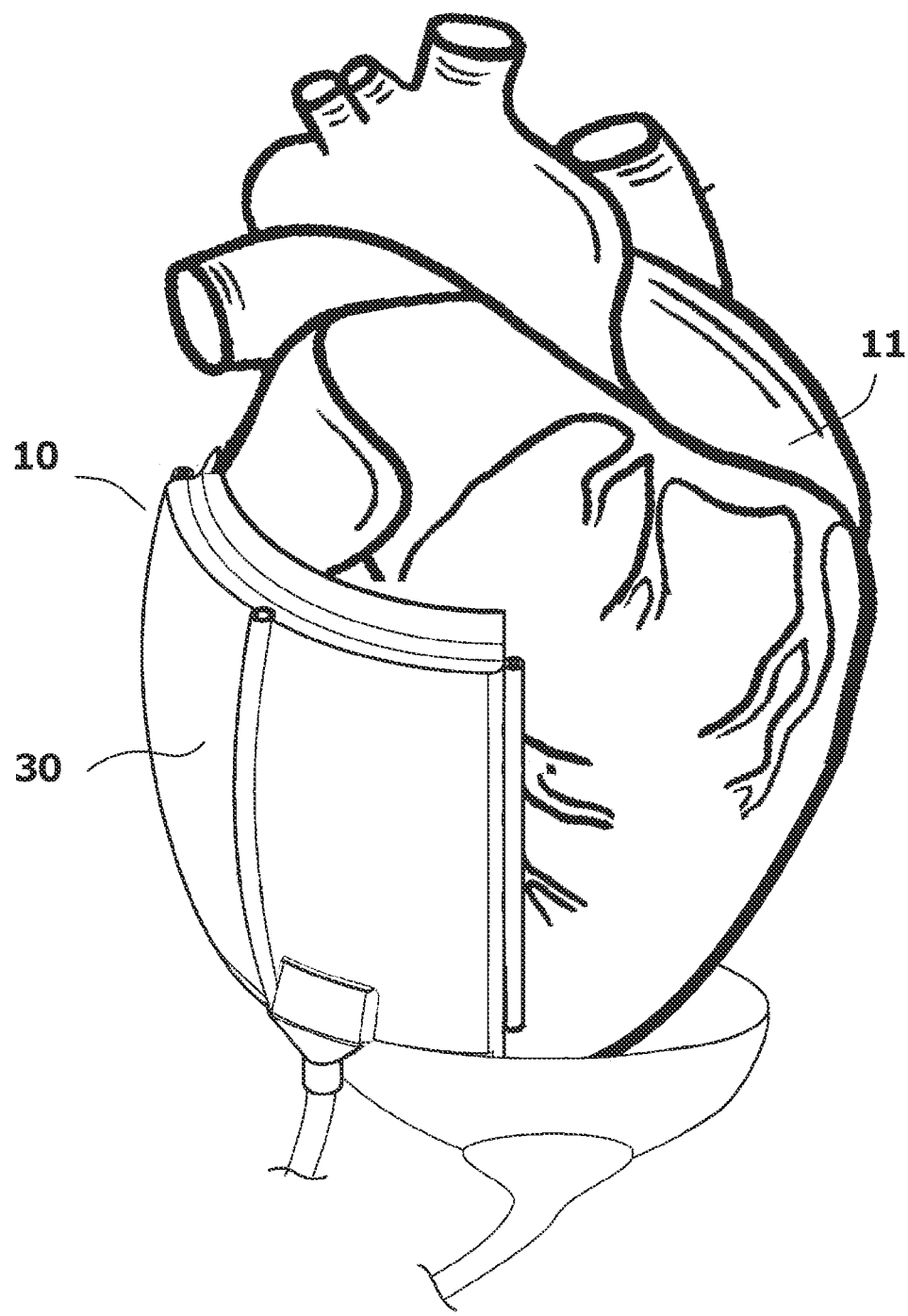
FIG. 11 shows a partial assembly applied to the heart.

Referring to FIG. 11, it will be understood that a heart 11 may have scar tissue, bypass anomalies or other obstacles that may prevent components of a heart pump from fully encircling the ventricles of the heart 11. There are also medical scenarios where the heart's pumping function is best served by assisting only the left ventricle or the right ventricle. In both cases, the heart pump system 10 can be configured to only partially encircle the heart 11. In FIG. 11, it can be seen that only one or two active panels 30 can be installed around the heart 11 using the installation methodology previously described.

The space available about a heart for a heart pump is difficult to ascertain prior to surgery. Scar tissue caused by disease, infection, or prior surgical procedures can limit the amount of space available. Using the methodology described, the space available for a heart pump system does not become fully known until the installation process is commenced.

Figure 12:
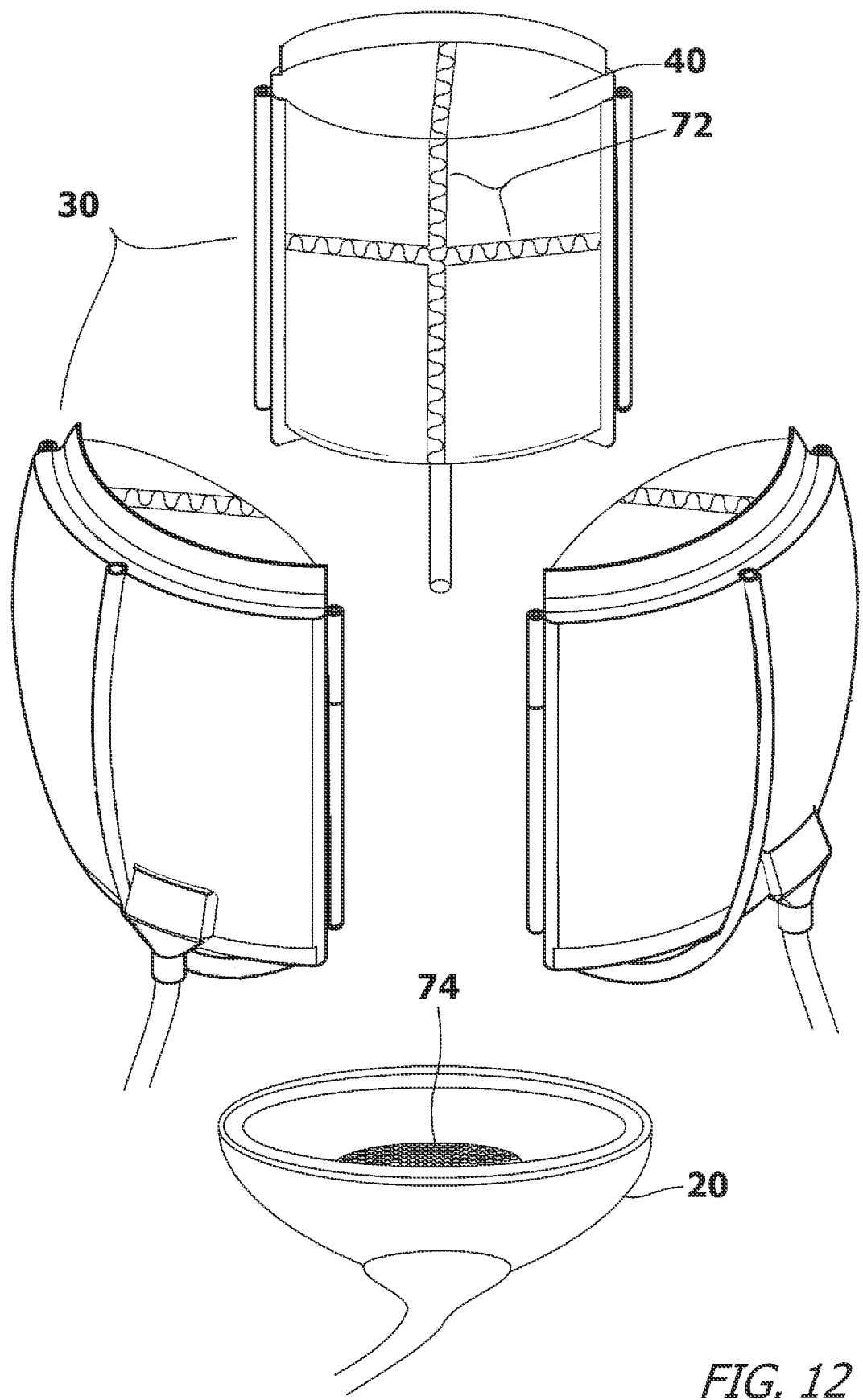
FIG. 12 shows an alternate embodiment of components of a heart pump containing optional electronic instrumentation.

It has been previously mentioned that a strain sensor can be incorporated into the panel connector. Other electronic sensors and devices can be added to the modular system. Referring to FIG. 12, it can be seen that strain gauges 72 can be incorporated into the inflatable membranes 40 of the active panels 30. Such gauges 72 can measure strain in the inflatable membrane 40, and thus, the force being applied to the heart during pumping. In the shown embodiment, strain gauges 72 are positioned along the long axis and short axis of each inflatable membrane 40. In addition, an ultrasonic sensor head 74 or other similar imaging sensor can be incorporated into the apical hub 20.

Figure 13:
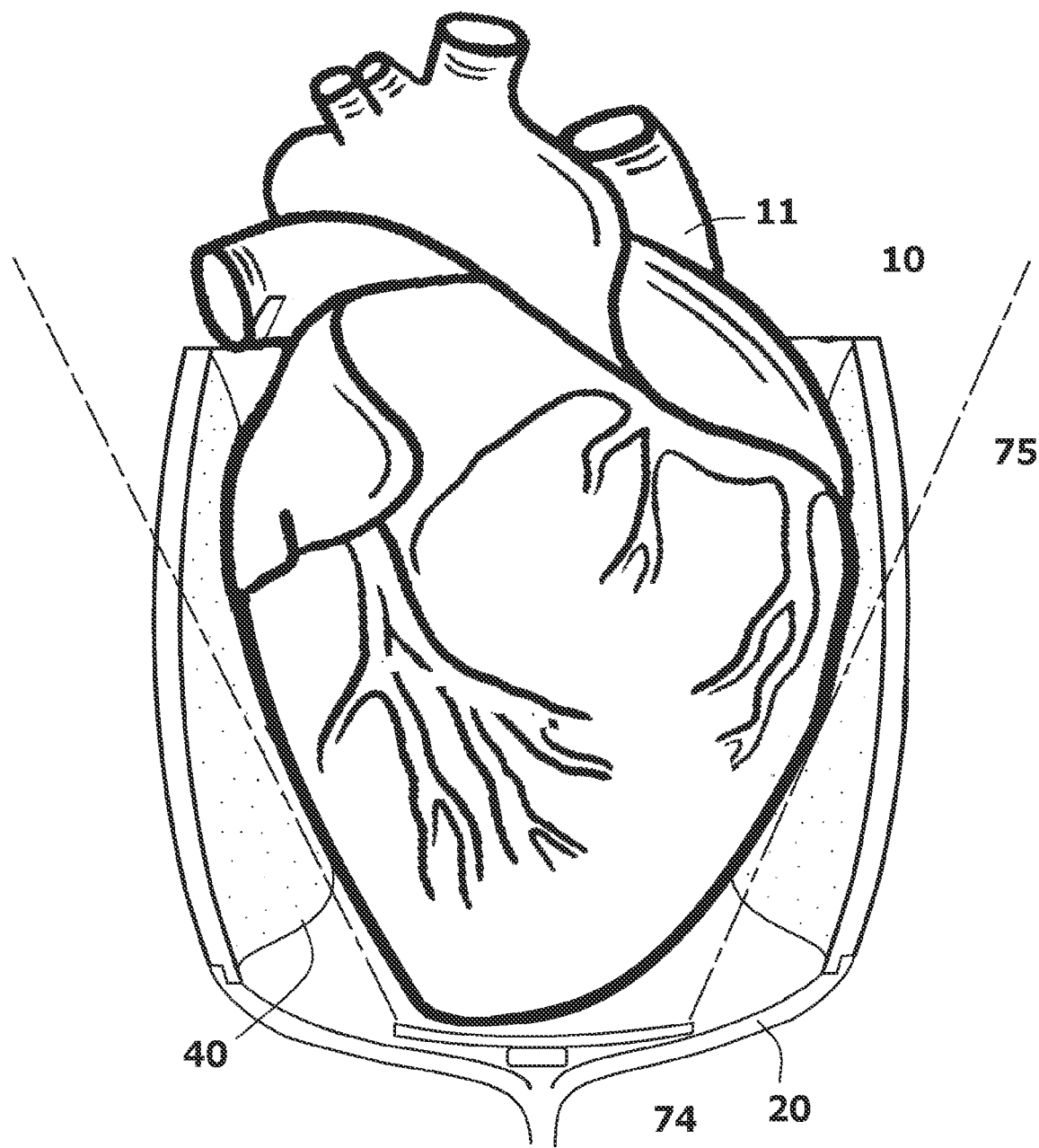
FIG. 13 shows the interrogation angles of the electronic instrumentation as the modular pump engages the heart.

Referring to FIG. 13 in conjunction with FIG. 12, it will be understood that since the apical hub 20 is biased against the heart 11 with suction, the ultrasonic sensor head 74 is ideally positioned to image the heart 11 along its long axis for as long as the heart pump system 10 is in place. Likewise, the ultrasonic sensor head 74 has a detection zone 75 that can also sense the position and contours of the inflatable membranes 40. This data can be used directly or combined with the data from the strain gauges 72 to control the inflation and deflation of the inflatable membranes 40. In this manner, the heart pump system 10 can properly translate forces to the heart and result in ventricular strain dynamics that benefit pump function and myocardial recovery. Furthermore, due to the ideal position of the ultrasonic sensor head 74, the imaging sensor 74 can be used to image the movements of the heart and the flow of blood within the heart. This enables the imaging sensor 74 to measure ventricular wall motion blood flow, valve efficiency and other aspects of heart function through the full pumping cycle.

Figure 14:
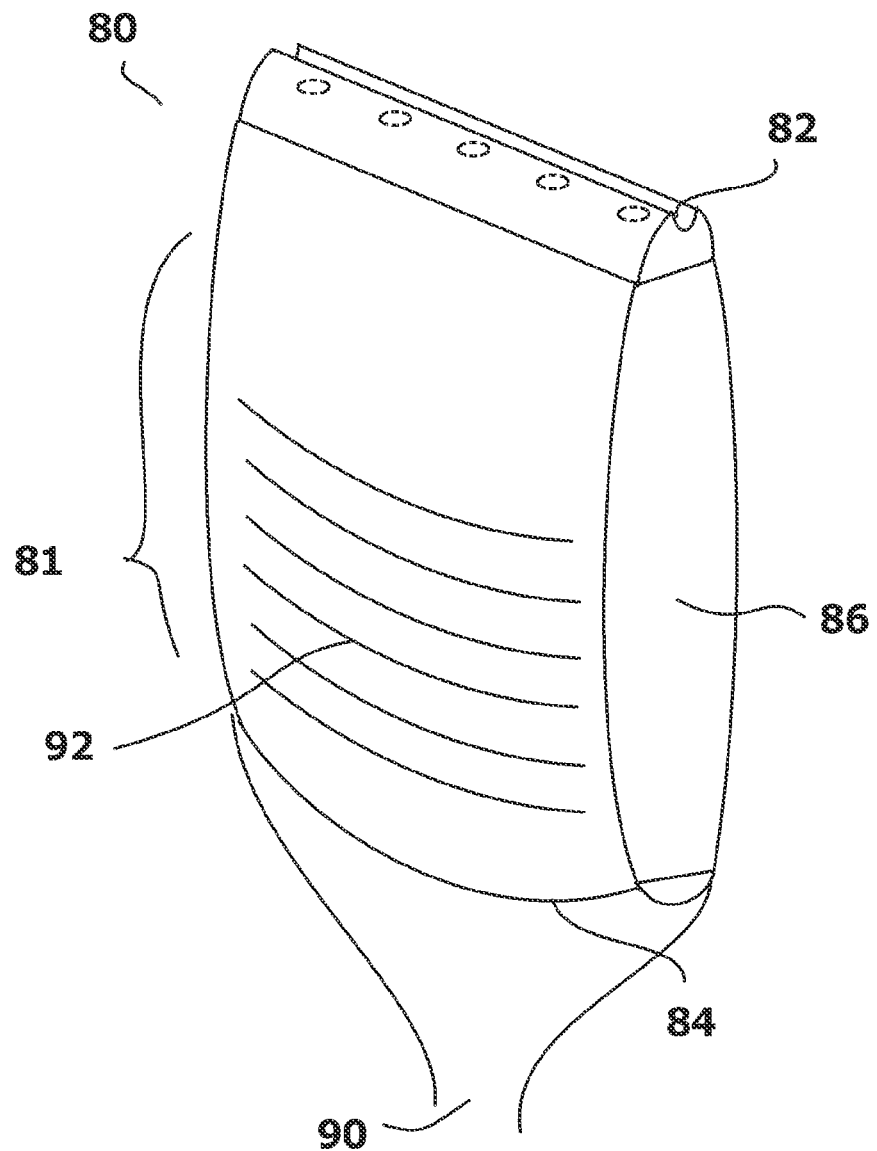
FIG. 14 shows an exemplary embodiment of a spacer tool used to measure and create space around the heart for the heart pump assembly, and measuring assembly.
Figure 15:
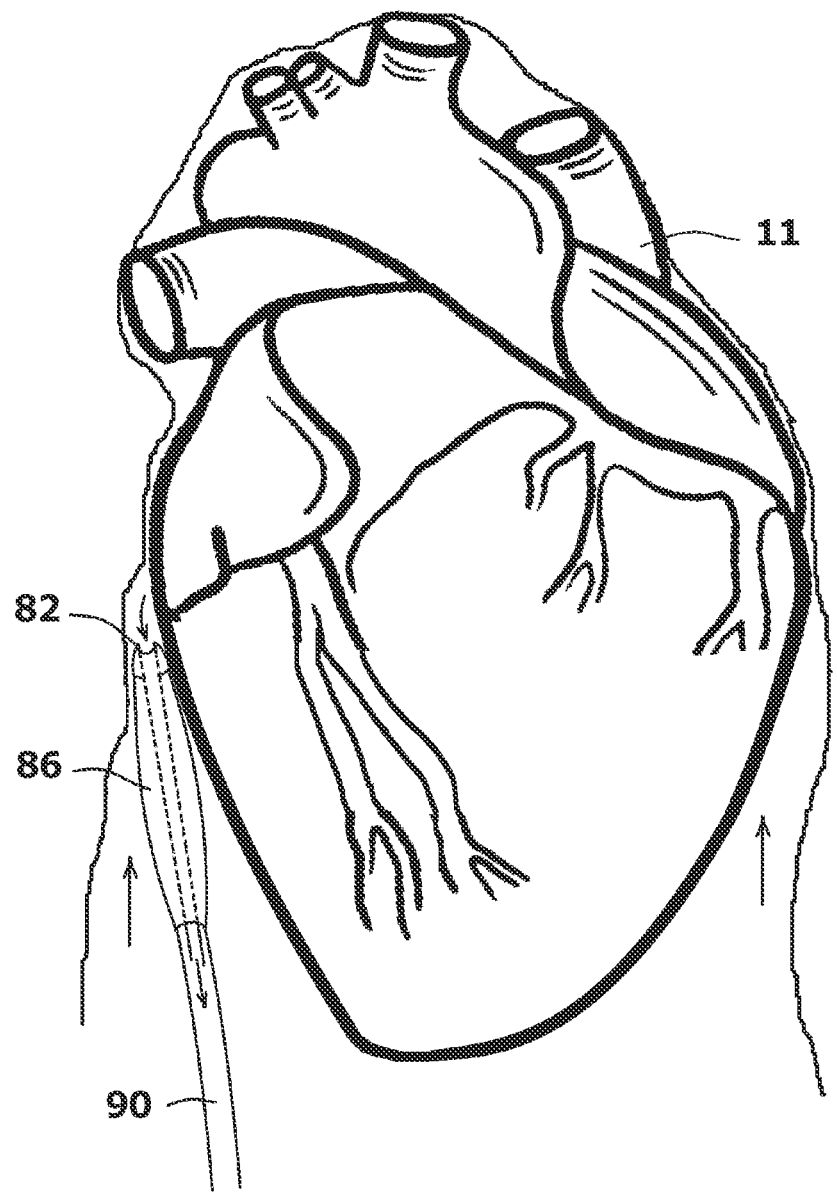
FIG. 15 shows the spacer tool assembly of FIG. 14 being advanced along the exterior of the heart.

Referring to FIG. 14 and FIG. 15, an assembly for use in an alternate methodology is shown. In FIG. 14 and FIG. 15, a spacer instrument 80 is shown. The spacer instrument 80 has a head 81 that can be position against the heart 11 and advanced up along the exterior of the heart 11. The head 81 of the spacer instrument 80 has a top edge 82, a bottom edge 84, and an elastomeric body 86. Suction openings 88 are formed on the top edge 82 of the elastomeric body 86 that connect to a suction tube 90. The elastomeric body 86 may contain grid scale markings 92 that can be readily seen on an x-ray medical viewing system. In addition, the elastomeric body 86 may have the ability to be selectively inflated and deflated to some degree to help displace fluid and tissue that may be disposed around the heart 11.

The spacer instrument 80 is positioned next to the heart 11. The elastomeric body 86 of the spacer instrument 80 is then advanced along the exterior of the heart 11 to determine the presence of scar tissue and other obstacles that may be present around the heart 11. As the spacer instrument 80 is advanced along the heart 11, liquids are suctioned through the suction openings 88. Furthermore, the elastomeric body 86 can be inflated and deflated to help the elastomeric body 86 pass through fluid and to dislodge small amounts of connective scar tissue that may be present.

Once the spacer instrument 80 is advanced fully, the level of advancement can be ascertained by viewing the grid scale markings 92 in relation to the position of the heart 11. Once the readings are made, the spacer ring assembly 80 can be moved to a different position on the heart 11 and the process is repeated. The readings gathered can then be used to determine what space is available around the heart 11. This information is then used to determine what size modular assembly should be used on the heart 11 and how many active panels should be included in the modular assembly.

It will be understood that the configurations of the present invention that are illustrated and described are merely exemplary and that a person skilled in the art can make many variations to those configurations. All such configurations are intended to be included within the scope of the present invention as defined by the claims.

What is claimed is:

1. A method of forming a heart pump about ventricles of a heart, comprising:

providing at least one active panel having a top edge, a suction tube, and an intake opening along said top edge that leads to said suction tube, wherein each said active panel includes an inflatable membrane;

positioning said at least one active panel in abutment with the heart;

providing an apical hub;

engaging said at least one active panel with said apical hub in vivo to form an assembly on the heart that at least partially encircles the ventricles of the heart.

2. The method according to claim 1, further including attaching said at least one active panel to a source of pneumatic pressure.

3. The method according to claim 1, further including attaching said apical hub to a source of negative pneumatic pressure.

4. The method according to claim 1, wherein said at least one active panel includes a plurality of active panels, wherein said method further includes joining said plurality of active panels together about the heart.

5. The method according to claim 4, wherein joining said plurality of active panels together includes joining said plurality of active panels together using panel connectors.

6. The method according to claim 5, wherein said panel connectors contain strain sensors that measure strain in said panel connectors.

7. The method according to claim 5, wherein providing at least one active panel includes providing at least one active panel having side edges and conduits proximate said side edges.

8. The method according to claim 7, wherein each of said panel connectors contains two pins that extend through said conduits on two of said plurality of said active panels, therein joining two of said plurality of said active panels.

9. The method according to claim 8, wherein said two pins are interconnected by a bridge structure.

10. The method according to claim 9, wherein a gap space exists between each of said plurality of active panels joined by said panel connectors.

11. The method according to claim 10, further including providing a gap shield for covering said gap space, wherein said gap shield is supported by said bridge structure.

12. The method according to claim 1, wherein said apical hub is held in position on the heart through suction that is applied to the heart through the apical hub.

13. The method according to claim 1, further including moving said at least one active panel around the heart and suctioning material through said suction tube as said at least one active panel is moved.

14. A method of positioning a construct about ventricles of a heart, comprising:

providing at least one active panel, wherein each said active panel includes a top edge, and wherein at least one drain port is disposed along said top edge;

positioning said at least one active panel against the heart;

providing an apical hub;

engaging said at least one active panel with said apical hub in vivo;

advancing said at least one active panel along the ventricles of the heart while suctioning material out of the pericardial cavity through said drain port.

15. The method according to claim 14, wherein said at least one active panel contains an inflatable membrane and said method further includes cyclically inflating and deflating said inflatable membrane while advancing said at least one active panel along the ventricles of the heart.

16. The method according to claim 14, wherein said at least one active panel includes a plurality of active panels, wherein said method further includes joining said plurality of active panels together in vivo.

17. The method according to claim 16, wherein joining said plurality of active panels together includes joining said plurality of active panels together using panel connectors.

18. The method according to claim 17, wherein said panel connectors contain strain sensors that measure strain in said panel connectors.

19. The method according to claim 14, further including providing an imaging head on said apical hub that can image the heart.

20. A method of positioning a pump about the heart, comprising:

providing a modular heart pumping device having a plurality of separate and distinct parts that include a scanning head;

assembling said plurality of separate and distinct parts about the heart in vivo, wherein said modular pumping device at least partially encircles the heart and said scanning head is oriented to scan the heart when said modular heart pump is assembled about the heart; and connecting at least some of said plurality of separate and distinct parts to an external pressure drive.

21. The method according to claim 20, wherein said scanning head is an ultrasonic scanning head.

22. The method according to claim 20, wherein said plurality of separate and distinct parts includes an apical hub and active panels that engage said apical hub.

23. The method according to claim 20, wherein said scanning head is disposed in said apical hub.

24. A method of positioning a construct about ventricles of a heart, comprising:

providing at least one active panel with an inflatable membrane, wherein each said active panel includes a top edge, and wherein at least one drain port is disposed along said top edge;

positioning said at least one active panel against the heart;

cyclically inflating and deflating said inflatable membrane while advancing said at least one active panel along the ventricles of the heart while suctioning material out of the pericardial cavity through said drain port.

* * * * *